United States Patent [19]
Benz et al.

[11] Patent Number: 5,424,038
[45] Date of Patent: Jun. 13, 1995

[54] SPECIMEN COLLECTOR

[75] Inventors: Reinhard Benz; Rolf Benz, both of Basel, Switzerland

[73] Assignee: Sotax AG, Allschwil, Switzerland

[21] Appl. No.: 120,576

[22] Filed: Sep. 10, 1993

[30] Foreign Application Priority Data

Sep. 22, 1992 [CH] Switzerland .................. 2966/92

[51] Int. Cl.⁶ .................. G01N 13/00; G01N 1/18
[52] U.S. Cl. .................. 422/100; 422/102; 422/103; 435/293; 435/300; 73/863.71; 73/863.81; 73/863.83
[58] Field of Search .................. 422/100, 102, 103; 435/30, 300, 293; 73/863.71, 863.81, 863.83

[56] References Cited

U.S. PATENT DOCUMENTS

| | | | |
|---|---|---|---|
| 3,306,111 | 2/1967 | Ferrin | 73/422 |
| 3,346,024 | 10/1967 | Berman et al. | 141/25 |
| 4,158,694 | 6/1979 | Bischoff et al. | 422/81 |
| 4,873,057 | 10/1989 | Robertson | 422/75 |
| 4,920,056 | 4/1990 | Dasgupta | 436/50 |
| 5,127,278 | 7/1992 | Benz | 73/866 |

FOREIGN PATENT DOCUMENTS 3323615 1/1985 Germany .

Primary Examiner—Robert J. Warden
Assistant Examiner—N. Bhat
Attorney, Agent, or Firm—Michael J. Striker

[57] ABSTRACT

An arrangement for receiving and transferring liquid specimens has a plurality of receiving vessels each formed as a closed cell provided with two conduits including a first conduit open below and a second conduit open above into an interior of the cell, two pairs of connecting conduits, and a mechanical switching device which is bringable in three positions for each group of the cells so as to alternatingly tightly close the first and second conduits, connect the first and second conduits with the first pair of connecting conduits, and connect the first and second conduits with the second pair of connecting conduits.

8 Claims, 3 Drawing Sheets

SPECIMEN COLLECTOR

BACKGROUND OF THE INVENTION

The present invention relates to specimen collectors.

For series tests, or in other words, for series studies of physical and chemical reactions in or of liquid media, so-called specimen collectors are utilized. Such arrangements are used for example when it is necessary to test how fast an effective substance available in a pellet is converted into a liquid after the pellet has been introduced into the liquid. It is, for example, known to collect the specimens of such liquids with the effective substance in test-tube-like receiving vessels of a fractionating collector and later remove them from the vessels for further treatment, for example for measurement of the effective substance concentration. Such fractionating collectors have known disadvantages in that their capacity is limited by the number of the available test tubes and the test tubes must be removed from the arrangement for cleaning. Another arrangement is also known in which the specimens are transported by a multi-position valve so that the volumes to be tested are supplied in a loop. Then they can be withdrawn from the device for further treatment. The devices which operate in this manner cannot, however, be used when the treatment time is longer than the test interval time.

SUMMARY OF THE INVENTION

Accordingly, it is an object of the present invention to provide a specimen collector which avoids the disadvantages of the prior art.

In keeping with these objects and with others which will become apparent hereinafter, one feature of the present invention resides, briefly stated, in an arrangement for receiving and transferring liquid specimens provided with several receiving vessels, wherein in accordance with the present invention, each receiving vessel is formed as a closed cell provided with two conduits which include a first conduit opening below and a second conduit opening above into the interior of the cell, and also there is a mechanical switching device which is movable between three positions so that for one group of cells it alternatingly tightly closes both conduits, or is connected to a first connecting conduit pair, or is connected to a second connecting conduit pair.

When the specimen collector is designed in accordance with the present invention, it avoids the disadvantages of the prior art and provides simultaneously three important properties. On the one hand, completely automatic serial tests can be conducted, or in other words testing in which no operating personnel is needed for exchanging and washing the receiving vessel. On the other hand, it is possible to conduct test series when the withdrawal intervals, or in other words the time intervals between the specimen withdrawals, are substantially shorter than the treatment time or the time required for measurements or physical or chemical conversions. Thirdly, no capacity limitations apply in this case.

In accordance with another advantageous feature of the present invention, the arrangement has a drain passage and a conduit connection for air, pressure air, and water; the cells are assembled into between three and twelve identical cell blocks, a switching device having a slider is associated with each of the cell blocks, and each of the blocks has up to fourteen cells; a multi-position valve having a number of inlet connections corresponding to a number of the cells in each cell block; a plurality of connecting systems each provided with the four connecting conduits and corresponding to the number of the cells per each cell block; the first connecting conduit of each connecting conduit system is a specimen liquid supply conduit which contains a feed pump and is connected only in the first switching position with the first conduit of the cell of the respective cell block associated with its conduit system; the second connecting conduit of each connecting conduit system is a specimen return conduit which only in the first switching position of the switching device is connected with the second conduit of the cell of the respective cell block associated with this connecting conduit system; the third connecting conduit of each connecting conduit system is a withdrawal or emptying conduit connected with the inlet connection of the multi-position valve, which only in the third switching position of the switching device is connected with the first conduit of the cell of the respective cell block associated with its conduit system, and a fourth one of the connecting conduits of each of the conduit systems is a supply conduit which only in the third position of the switching device is connected with the second conduit of the cell of the respective cell block associated with its conduit system; a control slider which is bringable into three positions and formed so that in the third position it connects the third connecting conduit of all the connecting conduit systems with the drain passage and connects the fourth connecting conduit with the conduit connection for air, pressure air, and water, in the second position it connects the fourth connecting conduit of all the conduit systems with the conduit connection for air, pressure air, and water, and in the first position it connects the first connecting conduit of all the connecting conduit systems with the drain passage and connects the second connecting conduit of all the connecting conduit systems with the conduit connection for air, pressure air, and water.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

A specimen collector in accordance with the present invention is formed in a shown embodiment as a transfer station. It includes five identical cell blocks 11,12,13,14 and 15 which are located near one another, a closure strip 10, and a control block 16. All the above-specified parts are assembled with one another by a not-shown frame or another auxiliary element.

Figure 1:
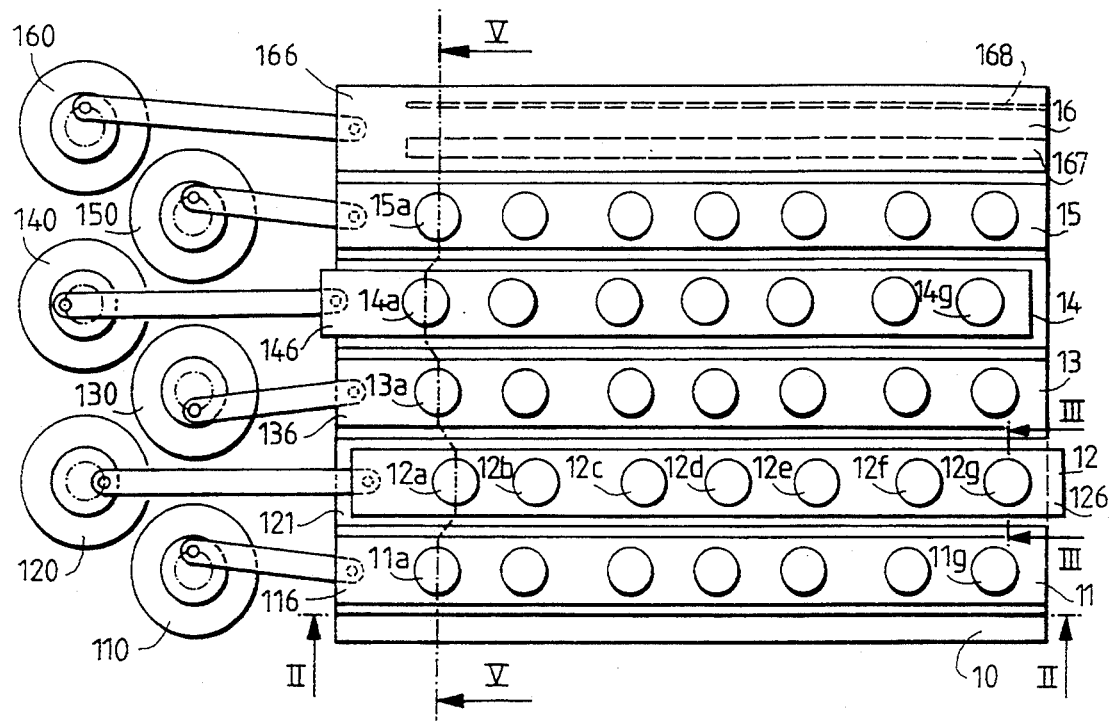
FIG. 1 is a schematic view of an arrangement in accordance with the present invention.
Figure 2:
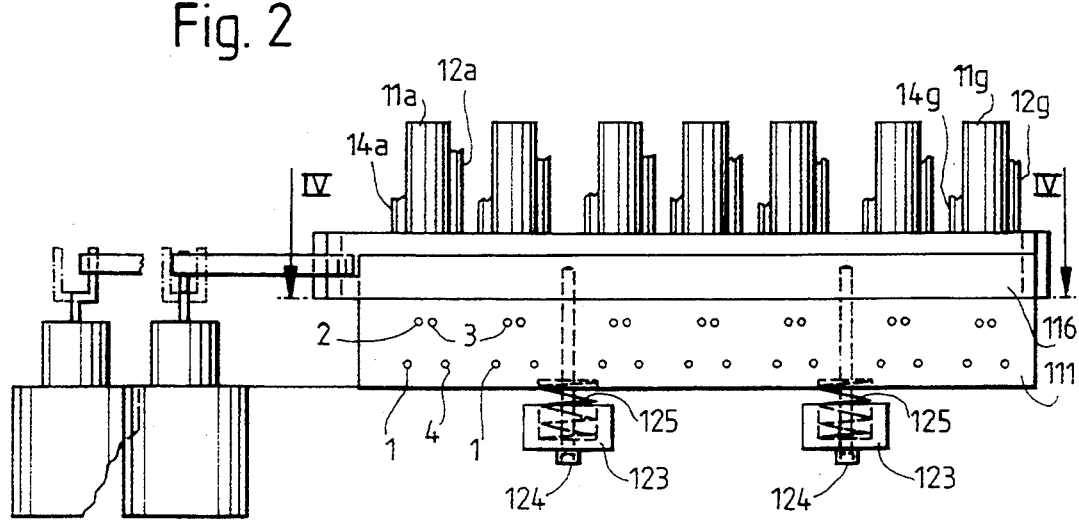
FIG. 2 is a view showing a section taken along the line II—II in FIG. 1.
Figure 3:
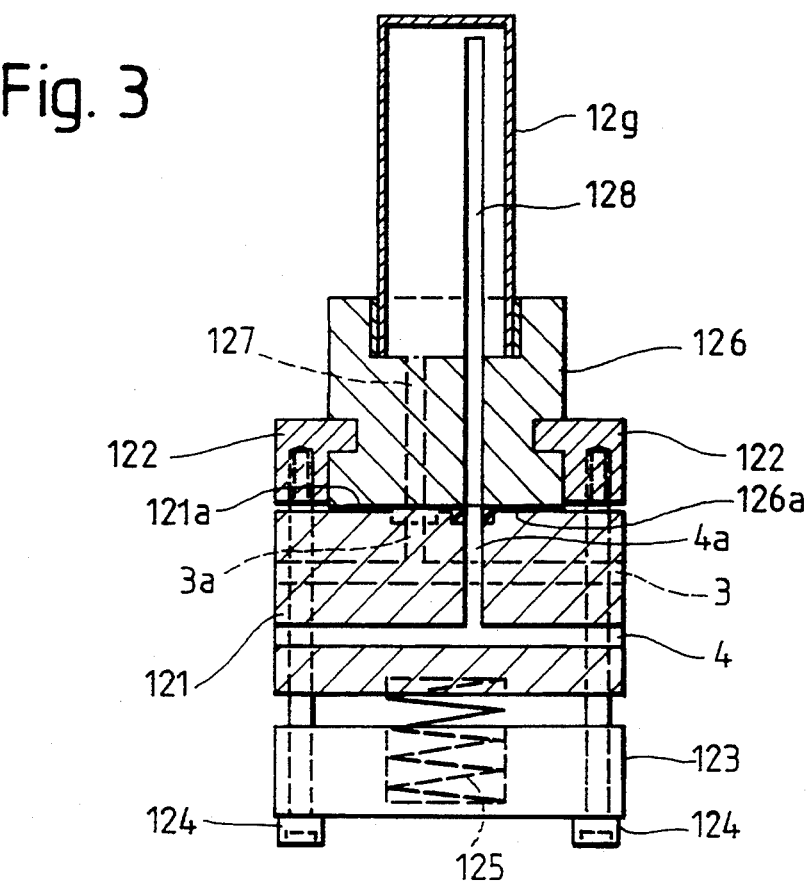
FIG. 3 is a view showing a section taken along the line III—III in FIG. 1 on an enlarged scale.

Each cell block, for example the cell block 12 shown in FIG. 3, includes a base element 121, two guiding rails 122, two bridges 123 whose arrangement is shown in FIG. 2, and also four screws 124 and four springs 125 which assemble these parts with one another. Each spring is associated with one bridge 123 and presses the latter from the base element 121 so as to pull both guiding rails 122 on the base 11. A slider 126 is displaceable in the guiding rails 122 in its longitudinal direction. Both springs 125 pull the slider 126 with its sliding surface 126a downwardly to the sliding surface 121a of the block 121, so that good contact between both sliding surfaces is provided. Seven closed cells 12a,12b,12c,12d,12e,12f and 12g are inserted in the slider 126. Each cell is provided with two conduits including the first conduit 127 which opens into the cell 12g from below and a second conduit 128 which opens into the cell 12g from above. The other end of the conduits 127 and 128, or in other words these mouths, are located in the sliding surface 126a of the slider 126.

In the base element 121 four horizontal openings extending transversely to the displacement direction of the slider 126 are provided per each cell. A vertical opening extends upwardly to a sliding surface 121a from each of these openings. All these openings together with the identical openings of the other four base elements together form seven conduit systems, or in other words a number of conduit systems corresponding to the number of cells per each cell block. Each conduit system includes four independent connecting conduits, each including a horizontal part composed of five portions and five vertical branches. For the sake of simplicity, in the drawings the four horizontal connecting conduits and also their conduit portions formed by the openings in the individual base elements for each of the seven conduit systems is identified with 1,2,3 and 4, while the associated vertical branches are identified with 1a,2a,3a and 4a correspondingly.

Figure 4:
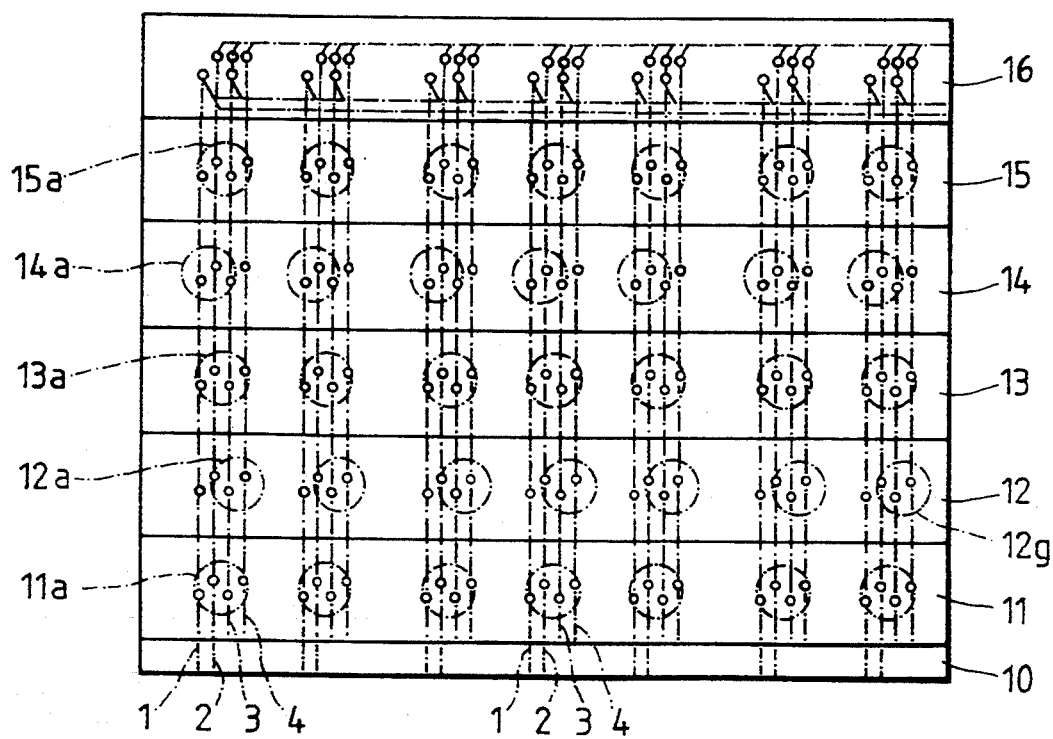
FIG. 4 is a view showing a section taken along the line IV—IV in FIG. 2.

As can be seen from the drawings, each slider 126 together with the associated base element 121 forms a switching device. The device serves for alternatingly connecting the first and the second conduit or in other words the conduits 127 and 128 of each cell of one cell block with two of the four connecting conduits of the corresponding conduit system. As can be seen in FIG. 4, in these positions the slider 126 connects both conduits of each cell with the connecting conduits 3 and 4 of the associated conduit system. In other words, it connects the first conduit 127 through the vertical branch 3a with the conduit 3 and the second conduit 128 through the vertical branch 4a with the conduit 4. The extreme position to the right in the drawings is identified in the subsequent description as a third position.

In the preceding position of the slider or in other words in the second position which corresponds to the position of the slider 126 in the cell block 13, the slider is located in the central position. In this position no conduits are located under the mouths of both conduits 127 and 128, and the cells are closed.

In the first position in which the slider 126 of the cell block 14 is shown, it is located in the left end position. In this position the first conduit 127 of each cell is connected with the connecting conduit 1 of the associated conduit system, and the second conduit 128 of each cell is connected with the connecting conduit 2 of the corresponding system.

As explained above, the arrangement has a control block 16 with a control slider 166 movable in three positions. A drain passage 167 and a supply connection 168 for air L, pressure air P, and water W are provided in the slider 166. The control block is designed so that in the first position it connects the first connecting conduit 1 of all conduit systems with the drain passage 167 and the second connecting conduit 2 of all conduit systems with the supply connection 168 for air L, pressure air P, and water W. In the second position it connects the fourth connecting conduit 4 of all conduit systems with the supply connection 168 for air L, pressure air P and water W, and in the third position it connects the third connecting conduit 3 of all conduit systems with the drain passage 167, but at the same time connects the fourth connecting conduit 4 with the supply connection 168 for air L, pressure air P and water W.

Figure 5:
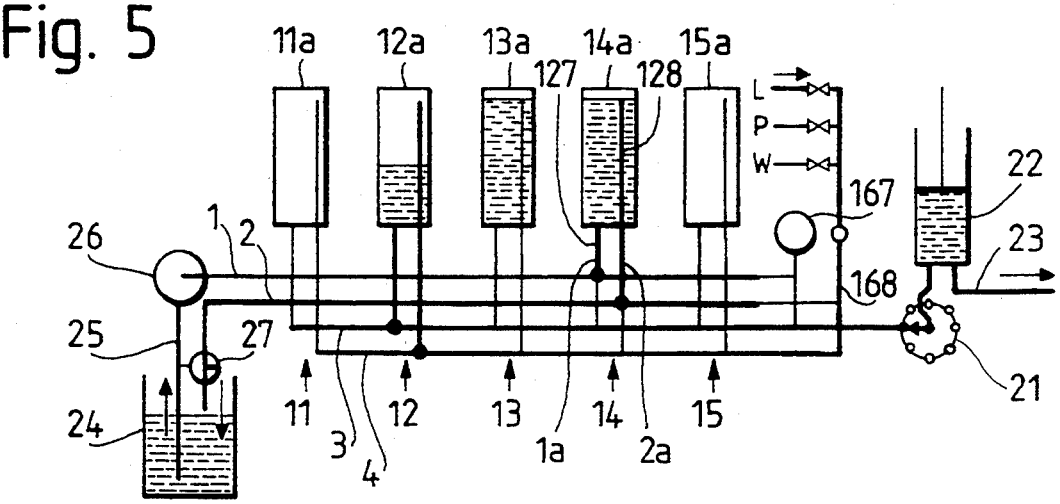
FIG. 5 is a schematic section taken along the line V—V in FIG. 1.
Figure 6:
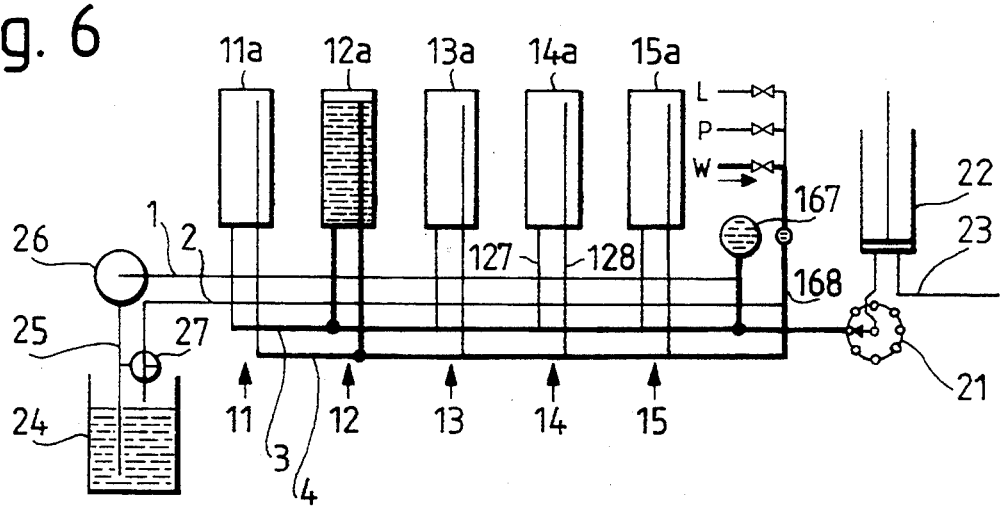
FIG. 6 is a view showing a section substantially corresponding to FIG. 5, but in another operational condition of the arrangement caused by another position of a control slider.
Figure 7:
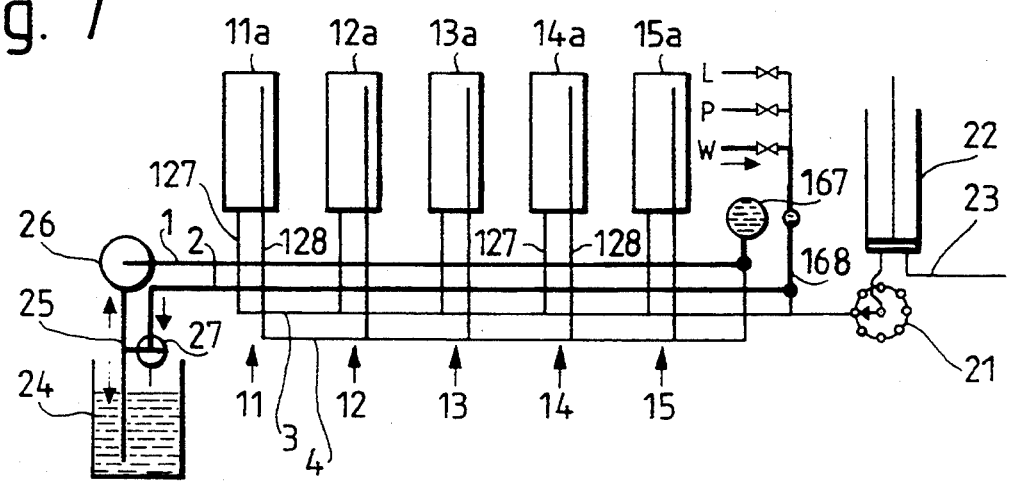
FIG. 7 is a view showing a section substantially corresponding to FIG. 5 but showing still another operational condition.

The inlet connections of the 8/1 valve 21 shown in FIGS. 5–7 are connected correspondingly with one of the seven connecting conduits 3 of the seven conduit systems. The individual outlet connections of this valve lead to a piston pump 22 or a displacing member performing the same action so as to aspirate selectively the fluid from one of the seven cells and transport it through a conduit 23 to a testing station.

In the embodiment shown in the drawings with the seven cells per cell block, it is possible to test the time conditions of seven pellets which are introduce a into a liquid and contain an effective substance. For this purpose seven containers which contain the testing liquid, each containing one pellet, are utilized. FIGS. 5–7 show one of the containers identified with reference numeral 24. One of the seven suction conduits 25 of the seven pumps 26 is introduced into each container 24 and the pumps can be driven from a single motor. At the pressure side each of the seven pumps is connected with one of the seven connecting conduits 1 which open into the connecting strip 10 and operate as a specimen liquid supply conduit. The connecting conduits 2 which operate as specimen return conduits are open in the connecting strip 10 and extend to the container 24, where each of them is connected through a three-way valve 27 with the corresponding suction conduit 25.

FIGS. 4 and 5 show the position of the slider during the withdrawal of the specimens from the container 24. First all cells of a cell block, or the cells 14a–14g of the block 14, are located in the filling and throughflow phase. In other words the slider 146 is located in the first switching position or in the left end position, and the control slider 166 is located in the central position or in the second position. Each of the seven pumps 26 transport the testing liquid from the associated container 24 through the associated testing fluid supply conduit 1 and the first conduit 127 of the corresponding cell into the cell, so that each of the seven cells of the cell block 12 is supplied with the specimen fluid from the associated container 24. When the cells are filled, further fluid flows through the second conduit 128 and the specimen return conduit 2 back into the container 24. It is therefore guaranteed that the specimens in the cells correspond to the condition in the associated container 24 or in other words in the testing vessel, and are not falsified by the end volume of the preceding specimen withdrawal. After a certain throughflow time, a motor 140 which is controlled by a not-shown electrical control displaces the slider 146 to the central position or in other words to the second switching position in which the slider 136 of the cell block 13 and its motor 130 are shown in the drawings. This is the waiting position in which both conduits of all cells of the cell block are closed. After this, a second actuation of the motor is performed, so that the slider assumes the position in which the motor 120 and the slider 126 are shown. In this position the first conduit 127 of each cell is connected with a third connecting conduit 3 and the second conduit 128 of each cell is connected with a fourth connecting conduit or in other words with the supply conduit 4 of the associated conduit system. It is connected in this operational position with the conduit connection 168 for air L, pressure air P and water W, which in turn is connected with the air supply L. Depending on the position of the 8/1 valve 21, the liquid can be withdrawn by the piston pump 22 from one of the seven cells 12a,12b,12c,12d,12e,12f,12g of the cell block 12 and supplied through the conduit 23 to a measuring or testing apparatus. Since the connecting conduit 4 is connected with the air supply L, air can flow into the emptying cell.

Usually the programming is adjusted so that the withdrawal from the seven cells follows one after the other so that the measuring or testing apparatus which provides through the conduit 23 with the liquid specimen to be tested a command to the element actuating the piston pump 22 and the 8/1 valve 21, is supplied with the next specimen or in other words with the specimen from the neighboring cell of the same cell block. When the specimen is withdrawn from the last of the seven cells of a cell block, the control slider 166 is brought by the motor 160 to the third position or in other words into the end position, so that the arrangement is located in the position shown in FIG. 6. In this position, all cells of each cell block in which the slider is located at the right end of its displacement path, or here the cells of the block 12, are rinsed with water W from the supply 168. Naturally, cleaning agents can be added to the water. The water flows through the connecting conduit 14 and the conduit 128 and through the conduit 127 and the connecting conduit 3 to the discharge passage 167. Afterwards, the cells in the same slider position can be blown with pressure air P and dried. After this cleaning phase, the slider 126 and the control slider 166 are again displaced back to their central position, and therefore the supply and withdrawal of the corresponding cells are closed. The cells of this block are in the waiting position until by means of a switching clock or another programming device in accordance with a preliminarily fixed working cycle, a displacement of the slider 126 to the left is activated. Thereby each cell of the cell block is connected with a conduit pair 1/2 and the cells can be again filled in the throughflow process. At the end of a complete testing process, when for example no more changes are determined from the successive studies of the specimen liquid of the individual container 24, all conduit portions 1 and 2 of all seven conduit systems are automatically cleaned, by bringing the control slider 166 to its first position by means of the motor 160 or in other words by displacing it to the left as shown in FIG. 7. Therefore the cleaning water W flows from the conduit 168 through the connecting conduit 2 to the ⅜-way valve 27 and from there partially into the container 24 and partially through the pump 26 and the connecting conduit 1 to the discharge passage 167. It is naturally also possible, before the cleaning of the conduits 1 and 2, to perform again the above-described cleaning of the cells shown in FIG. 6.

It is believed to be clear that within the spirit of the invention various possibilities for the realization of the inventive construction are possible. For example, it is possible to change the number of the cell blocks. It is possible to provide, for example, only three cell blocks or to the contrary substantially more, for example, twelve cell blocks. Each cell block can have the same number of cells which can be, however, between 1 and 14. Another possibility is to make the cells very long and small, or in other words to use only a substantially longer conduit portion as a cell. It is not also necessary to open both conduits of the cell into the sliding surface located under the cell. The slider can be guided between two sliding surfaces, an upper and a lower sliding surface, and the same conduit which opens in the cell from above can lead to the upper sliding surface. As a result the connecting conduits 2 and 4 can be arranged in the region above this sliding surface.

In the above-described examples, the arrangement is utilized for the testing of the time process of dissolving an effective substance in a liquid, wherein seven containers 24 operating as testing vessels are utilized, a pellet is dissolved in each of the containers, and for example each quarter hour from each of the seven parallel testing vessels a specimen is simultaneously supplied through seven parallel conduits of a cell block. It is, however, possible to supply all specimens through a single supply conduit by a pump with a multi-position valve with seven outlets. These outlets are in this case connected with the conduits 1 of the arrangement. Thereby the cells 11a–11g can be successively filled and then the cells of the neighboring cell block are filled. This is of course only one of numerous variants of the series tests which can be performed in the apparatus.

It will be understood that each of the elements described above, or two or more together, may also find a useful application in other types of constructions differing from the types described above.

While the invention has been illustrated and described as embodied in a specimen collector, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An arrangement for receiving and transferring liquid specimens, comprising a plurality of receiving vessels, each of said receiving vessels being formed as a closed cell provided with two conduits including a first conduit open below and a second conduit open above into an interior of said cell; two pairs of connecting conduits; mechanical switching means positionable in each group of cells in three positions so as to alternatingly tightly close said first and second conduits, to connect said first and second conduits with one of said of connecting conduits, and to connect said first and second conduits with the pair of connecting conduits; and means for connecting said first and second conduits with one of said pairs of connecting conduits and for connecting said first and second conduits with the other pair of connecting conduits.

2. An arrangement as defined in claim 1; and further comprising a drain passage and a conduit connection for air, pressure air, and water; said cells being assembled into between three and twelve identical cell blocks, said switching device having a slider and being associated with each of said cell blocks, and each of said blocks having one to fourteen cells; a multi-position valve having a number of inlet connections corresponding to a number of said cells in each cell block; a plurality of connecting systems each provided with said connecting conduits and corresponding to a number of said cells per each said cell block, so that a first one of said connecting conduits of each of said conduit systems is a specimen liquid supply conduit which contains a feed pump and is connected only in said first switching position with said first conduit of said cell of said respective cell block associated with its conduit system, a second one of said connecting conduits of each of said connecting conduit systems is a specimen return conduit which only in said first switching position of the switching device is connected with said second conduit of said cell of said respective cell block associated with said connecting conduit system, a third one of said connecting conduits of each of said connecting conduit systems is a withdrawal or emptying conduit connected with said inlet connection of said multi-position valve, which only in said third switching position of said switching device is connected with said first conduit of said cell of said respective cell block associated with its conduit system, and a fourth one of said connecting conduits of each of said conduit systems is a supply conduit which only in said third position of said switching device is connected with said second conduit of said cell of said respective cell block associated with its conduit system.

3. An arrangement as defined in claim 2, wherein said mechanical switching means includes a control slider which is movable between said three position and formed so that in said third position it connects said third connecting conduit of all said connecting conduit systems with said drain passage and connects said fourth connecting conduit with said conduit connection for air, pressure air, and water, in said second position it connects said fourth connecting conduit of all said conduit systems with said conduit connection for air, pressure air, and water, and in said first position it connects said first connecting conduit of all said connecting conduit systems with said drain passage and connects said second connecting conduit of all said connecting conduit systems with said conduit connection for air, pressure air, and water.

4. An arrangement as defined in claim 1, wherein each of said switching devices has two parts including a block and a slider which abut against said block, is longitudinally displaceable on said block, and is provided with an actuating member for displacement of said slider, said block and said slider being provided with a plurality of openings having mouths arranged in a surface of one part facing another part so that said mouths are bringable over one another in pairs.

5. An arrangement as defined in claim 4, wherein each of said blocks has a plurality of horizontal openings extending transverse to a direction of the displacement of said slider and a plurality of further openings extending from said horizontal openings upwardly and having mouths at a surface facing said slider.

6. An arrangement as defined in claim 1, wherein each of said switching devices has a slider provided with two sliding surfaces which are guided between two stationary sliding surfaces; and further comprising a plurality of openings provided in said stationary sliding surfaces and in said sliding surfaces of the slider and arranged so that depending on a position of said slider, said openings on said sliding surfaces of said slider and said openings on said stationary sliding surfaces are connected with one another in pairs or are closed.

7. An arrangement as defined in claim 4, wherein said cells are assembled in cell blocks, all said cells of one of said cell blocks being located in an upper surface of said slider, said first and second conduits ending in a lower surface of said slider.

8. An arrangement as defined in claim 4, wherein said cells are assembled in cell blocks, all said cells of one of said cell blocks being arranged on an upper surface of said slider, said first and second conduits ending in a lower surface of said slider.

* * * * *